(12) United States Patent
Forrer et al.

(10) Patent No.: US 9,925,522 B2
(45) Date of Patent: Mar. 27, 2018

(54) DOPED MATERIALS FOR REVERSE PHASE CHROMATOGRAPHY

(71) Applicant: ZEOCHEM AG, Ruti (CH)

(72) Inventors: Nicola Forrer, Glattpark (CH); Mandy Erdmann, Uznach (CH); David Gétaz, Ollon (CH); Massimo Morbidelle, Zürich (CH); Susanna Bernardi, Potenza Picena (CH); Rushd Khalaf, Zürich (CH)

(73) Assignee: ZEOCHEM AG, Ruti (CH)

( * ) Notice: Subject to any disclaimer, the term of this patent is extended or adjusted under 35 U.S.C. 154(b) by 564 days.

(21) Appl. No.: 14/387,363

(22) PCT Filed: Mar. 21, 2013

(86) PCT No.: PCT/CH2013/000050
§ 371 (c)(1),
(2) Date: Sep. 23, 2014

(87) PCT Pub. No.: WO2013/143012
PCT Pub. Date: Oct. 3, 2013

(65) Prior Publication Data
US 2015/0087816 A1    Mar. 26, 2015

(30) Foreign Application Priority Data
Mar. 28, 2012   (CH) .......................... 439/12

(51) Int. Cl.
*B01J 20/287*   (2006.01)
*B01J 20/288*   (2006.01)
(Continued)

(52) U.S. Cl.
CPC .......... *B01J 20/288* (2013.01); *B01D 15/325* (2013.01); *B01J 20/287* (2013.01);
(Continued)

(58) Field of Classification Search
None
See application file for complete search history.

(56) References Cited

U.S. PATENT DOCUMENTS

| 7,125,488 B2 | 10/2006 | Li |
| 2006/0076296 A1 | 4/2006 | Chen |

FOREIGN PATENT DOCUMENTS

| CN | 1759931 A | 4/2006 |
| CN | 101829551 A | 9/2010 |

(Continued)

OTHER PUBLICATIONS

"WO2011012019 Machine Translation.pdf"—machine translation of WO 2011/012019 specification (corresponds to Foreign Cite No. 6 on applicant's IDS dated Sep. 23, 2014)—Liang et al—Feb. 3, 2011.*

(Continued)

*Primary Examiner* — Krishnan S Menon
*Assistant Examiner* — Bradley R Spies
(74) *Attorney, Agent, or Firm* — Banner & Witcoff, Ltd.

(57) ABSTRACT

A material for reverse phase chromatography comprises surface modifying apolar and charged groups bound to a solid support, said charged groups being present in amounts of about 0.25 to about 22% of the surface modifying groups, or in amounts of about 0.01 $\mu mol/m^2$ to 0.8 $\mu mol/m^2$ referred to the surface of the solid support for a material with a total amount of surface modifying groups of 3.6 $\mu mol/m^2$. Such material and suitable purification conditions for active pharmaceutical ingredients (APIs) like peptides can be evaluated by (a) determining the isoelectric point (pI) of the API of interest, (b) choosing a pH in a range where the solid phase material is stable, (c) determining the difference pI−pH and (d) if the difference pI−pH is positive, choosing an anion (Continued)

exchange (AIEX) material, or if the difference pI–pH is negative, choosing an cation exchange (CIEX) material.

21 Claims, 11 Drawing Sheets

(51) Int. Cl.
 *B01J 20/32* (2006.01)
 *C07K 1/20* (2006.01)
 *B01D 15/32* (2006.01)
 *C07F 7/18* (2006.01)

(52) U.S. Cl.
 CPC ......... *B01J 20/3257* (2013.01); *C07F 7/1836* (2013.01); *C07K 1/20* (2013.01); *B01J 2220/80* (2013.01)

(56) References Cited

FOREIGN PATENT DOCUMENTS

| CN | 101987293 A | 3/2011 |
|---|---|---|
| GB | 2074892 A | 11/1981 |
| GB | 2431399 A | 4/2007 |
| WO | 9009238 A1 | 8/1990 |
| WO | 2011012019 A1 | 2/2011 |
| WO | 2011046494 A1 | 4/2011 |

OTHER PUBLICATIONS

"State-of-the-art in immobilized polymer.pdf"—J. Braz. Chem. Soc.—Faria, Anizio et al—Aug. 31, 2009.*
Fairbank, R.W. Peter et al.: 'Role of surface-adsorbed water in the horizontal polymerization of trichlorosilanes,' Journal of Chromatography A, 1999, pp. 285-291, vol. 830, Elsevier Science B.V.
Li, Li et al.: 'Studies of retention and stability of a horizontally polymerized bonded phase for reversed-phase liquid chromatography,' Journal of Chromatography A, 2000, pp. 153-167, vol. 868, Elsevier Science B.V.
Neue, Uwe D.: 'HPLC Columns: Theory, Technology, and Practice', 1997, pp. 191-196, Wiley-VCH, Inc.
Vansant, E.F. et al.: 'Characterization and Chemical Modification of the Silica Surface', 1995, pp. 149-158, Elsevier Science B.V.
Scott, R.P.W.: 'Silica Gel and Bonded Phases, Their Production, Properties and Use in LC', 1993, pp. 139-156, John Wiley & Sons.
Alpert, Andrew J.: 'Electrostatic Repulsion Hydrophilic Interaction Chromatography for Isocratic Separation of Charged Solutes and Selective Isolation of Phosphopeptides,' Analytical Chemistry, Jan. 1, 2008, pp. 62-76, vol. 80, American Chemical Society.
Nogueira, R. et al.: 'Alternative high-performance liquid chromatographic peptide separation and purification concept using a new mixed-mode reversed-phase/weak anion-exchange type stationary phase,' Journal of Chromatography A, 2005, pp. 158-169, vol. 1089, Elsevier B.V.
Umemura, Tomonari et al.: 'Amphoteric surfactant-modified stationary phase for the reversed-phase high-performance liquid chromatographic separation of nucleosides and their bases by elution with water,' Analytica Chimica Acta, 2000, pp. 87-92, vol. 419, Elsevier B.V.
Pettersson, Sylvia Winkel et al.: 'RP-HPLC Purification of Peptides and Proteins—Investigating the Benefit of Alternative Stationary Phases,' SPICA, Sep. 2010, pp. 1-23, Kromasil.
International Search Report dated Jul. 9, 2013 (PCT/CH2013/000050); ISA/EP.
Jie Wei et al: "A new reversed-phase/strong anion-exchange mixed-mode stationary phase based on polar-copolymerized approach and its application in the enrichment of aristolochic acids", Journal of Chromatography, vol. 1246, Mar. 22, 2012 (Mar. 22, 2012), pp. 129-136.
Crowther, Jonathan B. et al.: "High-Performance Liquid Chromatographic Separation of Oligonucleotides and Other Nucleic Acid Constituents on Multifunctional Stationary Phases", Journal of Chromatography, Elsevier Science Publishers B.V., Amsterdam, NL, vol. 282, Dec. 30, 1983, (Dec. 30, 1983), pp. 619-628.

* cited by examiner

DOPED MATERIALS FOR REVERSE PHASE CHROMATOGRAPHY

CROSS-REFERENCE TO RELATED APPLICATIONS

The present application is the U.S. National Phase of International Application No. PCT/CH2013/000050, filed on Mar. 21, 2013, designating the United States of America and claiming priority to Swiss Patent Application 439/12, filed Mar. 28, 2012, and this U.S. national phase application claims priority to and the benefit of the above-identified applications, each of which is incorporated by reference herein in its entirety.

TECHNICAL FIELD

The present invention regards the field of purification of active pharmaceutical ingredients like peptides by means of chromatography, in particular silica gel based materials for reverse phase chromatography.

BACKGROUND ART

Reverse phase chromatography is a broadly used purification method for peptides. Several materials to be used as the stationary phase in liquid chromatography comprise a support or carrier and thereon attached functional groups. Such material is also known as bonded phase. A commonly used carrier is silica gel that may suitably be surface modified by means of suitable silanes. The chemistry of silanes with various surfaces is well studied. A general discussion of the reaction of silanes with the surface of silicaceous chromatographic support materials is provided in HPLC Columns: Theory Technology, and Practice, U. D. Neue, Wiley-VCH, Inc., New York (1997). Additional details on the reaction of silanes with porous silicas are disclosed in Characterization and Chemical Modification of the Silica Surface, E. F. Vansant, et al., Elsevier Science B.V. New York (1995). A broad description of the reactions of silanes with a variety of materials is given in Silica Gel and Bonded Phases, Their Production, Properties and Use in LC, R. P. W. Scott, John Wiley & Sons, New York (1993).

The preparation of bonded phases can be made using monofunctional, bifunctional and trifunctional silanes resulting in differently strong bonded layers.

Irrespective of whether mono- bi- or trifunctional silanes are used, it is not possible to react all the silanol groups with the silylating reagents, due to equilibrium reactions and steric hindrance. Almost complete coverage is only obtained if the silylating reagents are horizontally polymerised. It is reported that even with the most aggressive silanization reactions no more than 50% of the silanol groups can be converted to silylated derivatives.

Most commercially available bonded phases are based on monofunctional silanes because of difficulties in the reproducibility in preparing bonded phases using bi- and trifunctional silanes.

Since a significant portion of the original silanol groups remain, these may interact with silanophilic analytes unless they are shielded. A commonly used method to reduce these interactions is the so-called endcapping. Here a small monofunctional silane (e.g. trimethylchloro silane) is reacted with the silicagel surface to provide an additional coverage of the silicagel surface.

U.S. Pat. No. 7,125,488 B2 teaches to solve the hitherto existing problems by providing a polar modified stationary phase material, said material having an inorganic support such as silica gel that is modified with a specific silane providing the polar modification. The polar modifications comprise groups like —O—, —C(O)NH—, —OC(O)NH—, and —(CH$_2$CH$_2$O)$_n$—.

Recently, a strong focus on the development of stationary phases with bimodal chemical surface character has been made. Reversed-phase/ion-exchange (RP/IEX) mixed-mode stationary phases are known and promise great versatility and capability for retaining and separating a variety of charged polar compounds, in addition to more nonpolar, ionic and nonionic analytes. According to the arrangement of functional groups, RP/IEX bimodal columns can be classified into four categories. One type of materials is a mixture of RP and IEX beads. Another type of materials comprises apolar groups and polar groups like amines and carboxylic acids in similar amounts attached to the same bead, a third type of materials comprises apolar chains tipped with polar groups, and a fourth type of mixed-mode materials comprises an anionically or cationically charged group embedded within an apolar chain.

GB 2 074 892 A describes materials with mixed surfaces wherein one kind of ligands is selected from ionic or reversed phase ligands and the second kind is a hydrophilic group like a diol, a diol precursor or an amide.

Also GB 2 431 399 A discloses mixed surfaces with 2 different silyl moieties bonded thereto. Each of these silyl moieties comprises 2 C1-C6 alkyl chains and one further group. In a preferred embodiment said further group is an apolar group on one of the silyl groups and a polar group embedded in apolar chains on the other silyl group.

Also already known are trimodal columns based on nanopolymer silica hybrid technology. Such columns comprise Acclaim® Trinity™ P1 of Dionex. This material consists of high-purity porous spherical silica gel coated with charged (e.g. such as to have cation-exchange functionality) nanopolymer particles and with inner pore areas of the silica gel modified with an organic layer that provides RP and IEX properties.

Other mixed mode materials have been developed and are described under the trademark Kromasil™ (belonging to Akzo Nobel). These one particle-multiple resins stationary phases are described to comprise 50% or 25% of a different functionality like polar functionality (CN, NH2, diol). Although these phases provide better separation in several cases, they are still not satisfactory for a multitude of applications.

CN 101829551 A discloses chromatographic materials bonded with apolar ligands and anionic ligands for use in the separation of melamine from a milk sample and of several phytohormones. The density of anionic groups is disclosed to be 33 to 66%.

Also already known are materials with enhanced ligand density due to horizontal polymerization. These materials have been found to have much higher ligand density than merely grafted materials. First horizontally polymerized materials were described by Fairbank and Wirth, *Role of surface-adsorbed water in the horizontal polymerization of trichlorosilanes*, Journal of Chromatography A, 830 (1999) 285-291, and further investigated by Li, Carr and Evans, *Studies of retention and stability of a horizontally polymerized bonded phase for reversed-phase liquid chromatography*, Journal of Chromatography A, 868 (2000) 153-167. Adaptation of this technique to different kinds of ligands, i.e. apolar and polar ligands or apolar and ionic ligands is described in WO 2011/012019 and Wei et al., *A new reversed-phase/strong anion-exchange mixed-mode station-* ary phase based on polar-copolymerized approach and its application in the enrichment of aristolochic acids, Journal of Chromatography A, 1246 (2012) 129-136.

The problem with such horizontally polymerized materials is that a successful production is dependent on the adsorbed water and thus they have to be produced using a quite complicated procedure that renders them very expensive and thereby unsuitable for preparative applications. In addition, although such materials were successfully applied in the analytical enrichment of specific aristolochic acids, they failed in preparative application (Wei et al.)

Since the materials of the state of the art are either not satisfactory with regard to the quality of the separation and/or with regard to the retention time and/or—in particular if desired for preparative applications—with regard to their production costs, there still exists a need for improved materials.

DISCLOSURE OF THE INVENTION

Hence, it is a general object of the invention to provide a stationary phase material for reverse phase chromatography that is adapted to the purification or separation of specific active pharmaceutical ingredients (API), in particular to the preparative purification or separation of specific API.

It is another object of the present invention to provide a method that enables to choose a suitable stationary phase material and/or suitable elution conditions for API purification by reverse phase chromatography.

Now, in order to implement these and still further objects of the invention, which will become more readily apparent as the description proceeds, the material for reverse phase chromatography is manifested by the features that it comprises surface modifying groups bound to a solid support, said surface modifying groups are not horizontally polymerized and comprise apolar uncharged groups and polar groups, wherein said polar groups are charged groups, said charged groups are either positively charged or negatively charged, and said charged groups are present in amounts of about 0.25 to about 22% of the surface modifying groups, or in amounts of about 0.01 µmol/m$^2$ to 0.8 µmol/m$^2$ referred to the surface of the solid support for a material with a total amount of surface modifying groups (i.e. apolar uncharged groups and charged groups) of 3.6 µmol/m$^2$.

The total amount of surface modifying groups is determined by standard techniques like elemental analysis and the amounts of charged groups can be determined by ionic titration.

A material for reverse phase chromatography according to the present invention is also termed a doped material or a doped material for reverse phase chromatography or a doped reverse phase material, because it comprises the charged groups in small (doping) amounts of at most 22%, preferably at most 20% or 15% or 10%.

The doping effect seems best if the total surface coverage with apolar and charged groups is not too high, i.e. not as high as obtained with horizontal polymerization. This high surface coverage obtained with horizontal polymerization is assumed to possibly be responsible for the bad results in preparative separation experiments reported in Wei et al.

The term API as used herein designates molecules with apolar and charged groups, in particular peptides, preferably peptides with up to about 50 amino acids (aa).

Since the solid support as such is substantially shielded, any solid support known for chromatographic purposes can be used. Preferred, however, is silica gel due to the silanol groups on the surface that allow easy attaching of the modifying groups via reaction with e.g. silanes. Suitable silanes are e.g. monofunctional silanes like mono-chloro substituted silanes or trifunctional silanes like trimethoxy silanes. Presently, trimethoxy silanes are preferred since they are able to react with up to three neighboring silanol groups thereby shielding the silanol groups and simultaneously strengthening the anchoring of the modifying substituent. In addition, the surface proved to be sufficiently covered with substituents/surface modifying groups even if trifunctional silanes were used. In addition, hitherto reproducibility problems reported in the state of the art for trifunctional silanes were not observed.

Suitable silica gels are high purity silicagel with porosity of 50 to 300 Å, preferably about 100 Å, and particle sizes from 5 to 100 µm, preferably from 10 to 20 µm.

Preferred apolar uncharged groups are linear C4 to C18 alkyl groups, in particular C8 alkyl groups, although alkenyl and alkinyl groups can also be used. Alkyl groups are preferred since they have maximum freedom of movement.

The charged groups are preferably placed on aliphatic chains of shorter or similar length as the apolar groups to ensure that the charged groups do not dominate the uncharged, apolar groups. Shorter chains may e.g. be shorter for up to 6 CH2 groups, usually up to 5 CH2 groups, preferably 3 to 5 CH2 groups. Therefore, the hydrocarbon chains carrying a charged group may be C1 to C18 chains. Although it is known to embed charged groups into the hydrocarbon chain, presently terminal position or position at the tip of the hydrocarbon chain, respectively, of the substituents is preferred.

The charged substituents have the effect that they repel identically charged amino acids and attract oppositely charged amino acids. While the charge of the charged substituents is not critical, presently singly-charged substituents, like —NR$_3^+$ with R=hydrogen or C1-C2 alkyl, or —SO$_3^-$ are preferred over multiply charged substituents. Already singly charged substituents have sufficient effect in low amounts.

Dependent on the API to be purified and the separation conditions differently doped reversed phase materials may be suitable. The best material and API purification conditions can be selected by (a) determining the isoelectric point (pI) of the API of interest, (b) choosing a pH in a range where the solid phase material is stable, (c) determining the difference pI–pH and (d) if the difference pI–pH is positive (pI>pH), choosing an anion exchange (AIEX) material, or if the difference pI–pH is negative (pI<pH), choosing a cation exchange (CIEX) material.

Thus the present invention also encompasses (i) the use of a material for reverse phase chromatography comprising surface modifying groups bound to a solid support, said surface modifying groups comprising apolar uncharged groups and polar groups, wherein said polar groups are positively charged groups, in particular a positively charged material as defined above for reversed phase purification of an API, in particular a protein under conditions wherein pI>pH, and (ii) the use of a material for reverse phase chromatography comprising surface modifying groups bound to a solid support, said surface modifying groups comprising apolar uncharged groups and polar groups, wherein said polar groups are negatively charged groups, in particular a negatively charged material as defined above for reversed phase purification of an API, in particular a protein, under conditions wherein pI<pH.

Determining the isoelectric point encompasses the experimental determination, the calculation from the amino acid (aa) sequences, but also the search for respective information in literature or other sources comprising personal knowledge.

The pH should be chosen such that the lifetime of the material is not affected. For silica gel a pH between 3 and 9 is preferred, even more preferred is a pH between 4 and 7.

If a material has been chosen, a desired retention time can be fixed and then the eluting conditions can be adapted thereto by determining the ionic strength of the buffer and/or by determining the solvent system of the mobile phase (eluent system) and the gradient.

Possible eluent systems comprise or consist of at least one polar solvent, preferably a combination of water, such as water of a specific pH, and at least one further polar solvent having a polarity that is lower than the polarity of water. Such less polar solvents may e.g. be chosen from the group comprising or consisting of methanol, ethanol, isopropanol, tetrahydrofurane (thf), acetonitrile and combinations thereof. In a preferred embodiment, not simply water of a specific pH is used but a buffered aqueous solution.

One eluent system that has proved to be suitable for different separation applications is an aqueous buffer and acetonitrile. The starting composition and the end composition of the eluent system as well as the gradient can be found by usual routine methods.

BRIEF DESCRIPTION OF THE DRAWINGS

The invention will be better understood and objects other than those set forth above will become apparent when consideration is given to the following detailed description thereof. Such description makes reference to the annexed drawings, wherein:

FIG. 3 shows the effect of buffer concentration (FIG. 3a for 300 mM acetate, FIG. 3b for 500 mM acetate, FIG. 3c for 800 mM acetate) on the retention time of a positively charged API on various columns.

FIG. 4 shows the effect of modified acetonitrile gradient on retention time, wherein FIG. 4a shows the retention time of the specific columns using identical elution conditions while

MODES FOR CARRYING OUT THE INVENTION

According to the presently preferred method for surface modification, all surface modifying groups are attached simultaneously from a liquid solution comprising the apolar groups and the polar charged groups. Dependent on the substituents used it has been found that the reaction may more or less favor the charged or the apolar groups. Therefore the actually obtained material has to be determined by e.g. ionic titration.

It is also possible to perform the reaction in several steps, i.e. attachment of the apolar groups first, followed by the charged groups or vice versa. In this procedure, however, the reaction conditions have to be selected such that in the first step some available silanol groups are not reacted. In any case, also in a two (or more) step procedure the actually attached ionic groups have to be determined, e.g. by ionic titration.

The preferred and/or obtainable ranges of charged groups may vary from charged group to charged group. For $—SO_3^-$ the usual range is from 0.01 $\mu mol/m^2$ to 0.04 $\mu mol/m^2$ and for $—NR_3^+$ the usual range is from 0.01 $\mu mol/m^2$ to 0.8 $\mu mol/m^2$ although higher amounts can easily be produced (see examples below). Higher $—NR_3^+$-doped materials with e.g. R—$CH_3$, however, have been found to be less good (see FIGS. 3 and 4). The lower limit of the amount of ionic groups is the minimal number of doping ionic groups that has to be present for a visible effect. The upper limit is given by the strength or weakness, respectively, of the adsorption. Thus, higher than the indicated amounts of ionic groups might be used but with possibly worse separation and/or inadequate retention times.

The effect of the doping is that in case of a API that is positively charged (isoelectric point (pI–pH=positive, or pI>pH, respectively) the adsorption on an AIEX material, e.g. $—NR_3^+$ doped material, is weak (repulsion) and on a CIEX material, e.g. $—SO_3^-$ doped material, strong (attraction) and vice versa.

As indicated above, the apolar groups are preferably at least C4 groups and usually not larger than C18 groups with C8 groups being presently preferred. The charged groups encompass any charged substituent, preferably a charged substituent attached to a C1 to C18 hydrocarbon, more preferred a charged substituent attached to a hydrocarbon having slightly smaller or about the same length as the apolar chain. Due to the fact that the substituent is larger than a hydrogen, the charged substituent carrying group usually and preferably have a slightly sorter chain, e.g. C3 compared to C8 of the apolar group. Without wanting to reduce the scope of the invention by any interpretation, the inventors assume that attaching the ionic groups via a shorter hydrocarbon chain results in a weak shielding of the ionic groups and thus in a lower attraction or repulsion of the molecules in the analyte.

The invention is now further described by means of some examples:

Example 1

Several CIEX and AIEX materials have been prepared by subjecting them to compositions comprising the C8-compound octyltrimethoxysilane and (0%), 5%, 10%, 15% or 50% of $—SO_3^-$-charged or $—NR_3^+$-charged C3-compound according to standard procedures.

The $—NR_3^+$ materials (R=methyl) were produced by combining the desired amount of silicagel, octyltrimethoxysilane, N-trimethoxysilylpropyl-N,N,N-trimethylammonium chloride, and p-toluensulfonic acid (catalyst) and boiling under reflux in toluene for 6 hours.

The desired amounts were as follows:
Octyltrimethoxysilane in a concentration of $(1-x)*5.6*10^{-6}$ mol/m$^2$*$S*M*MWt$, wherein x is the desired weight percentage of —NR$_3^+$ groups,
S the specific surface of the silicagel [m$^2$/g],
M the mass of the silicagel used [g] and
MWt the molecular weight of octyltrimethoxysilane [g/mol].

N-trimethoxysilylpropyl-N,N,N-trimethylammonium chloride was used as a solution of 50% by weight of the silane in methanol and the amount solution used was $x*2g/g*M-x*2*M$, wherein x is the percentage of the —NR$_3^+$ groups as described above and
M is the mass of silicagel [g].

p-Toluensulfonic acid (catalyst) was used in a concentration of 8.6*10-3 g/g of octyltrimethoxysilane and N-trimethoxysilylpropyl-N,N,N-trimethylammonium chloride After 6 hours the material was endcapped, i.e. not reacted, still accessible silanol groups, were reacted with trimethylchloro silane by a standard technique and washed with a series of solvents with different polarities.

The —SO$_3^-$-materials were produced by combining the desired amount of silicagel, octyltrimethoxysilane, mercaptopropyltrimethoxysilane, and p-toluensulfonic acid, in toluene and boiling under reflux for 6 hours.

The desired amounts were as follows:
Octyltrimethoxysilane in a concentration of $(1 \times x)*5.6*10^{-6}$ mol/m$^2$*$S*M*MWt$, wherein x is the desired weight percentage of -SO$_3$- groups,
S is the specific surface of the silicagel [m$^2$/g],
M is the mass of silicagel used [g] and
MWt the molecular weight of the silane [g/mol].

Mercaptopropyltrimethoxysilane was used in a concentration of $x*5.6*10^{-6}$ mol/m$^2$*$S*M*MWt$, wherein x is the desired weight percentage of —SO$_3^-$ groups,
S the specific surface of the silicagel [m$^2$/g],
M the mass of silicagel used [g] and
MWt the molecular weight of the silane [g/mol].

p-Toluensulfonic acid was used in a concentration of $8.6*10^{-3}$ g/g of the total amount of octyltrimethoxysilane and mercaptopropyltrimethoxysilane used.

The material was then endcapped by the use of standard techniques and washed with a series of solvent with different polarity.

—SO$_3^-$ groups were created by oxydizing the mercapto group as follows: The material was put in a solution of 30% by volume acetone in H$_2$O$_2$ (30% by weight in water) and kept in the solution for 12 hours at room temperature. Finally the material was washed with water and methanol.

Figure 1:
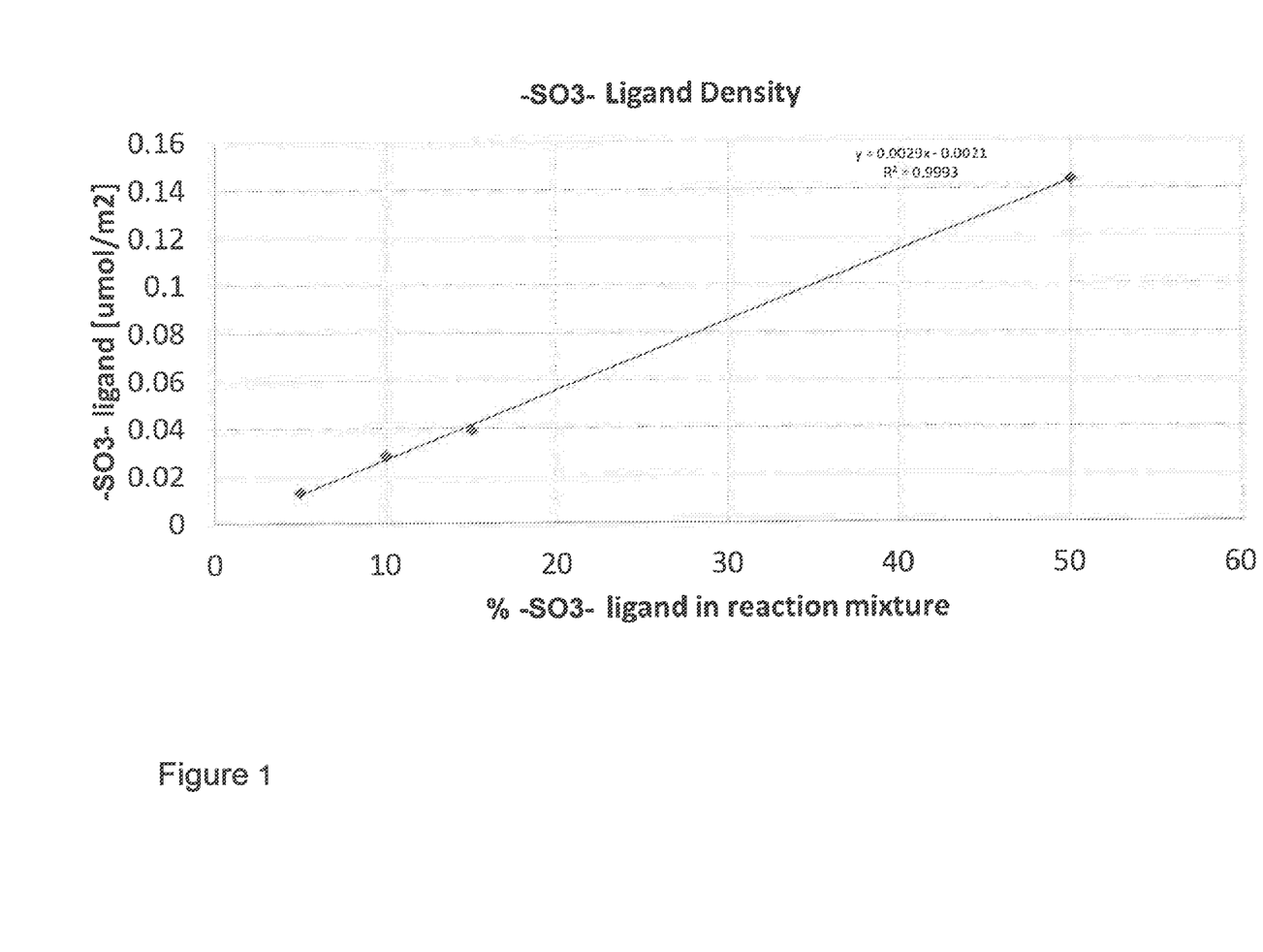
FIG. 1 shows a correlation between anionic functional group ($—SO_3^-$) in the reaction mixture and anionic functional group attached to the silica gel.
Figure 2:
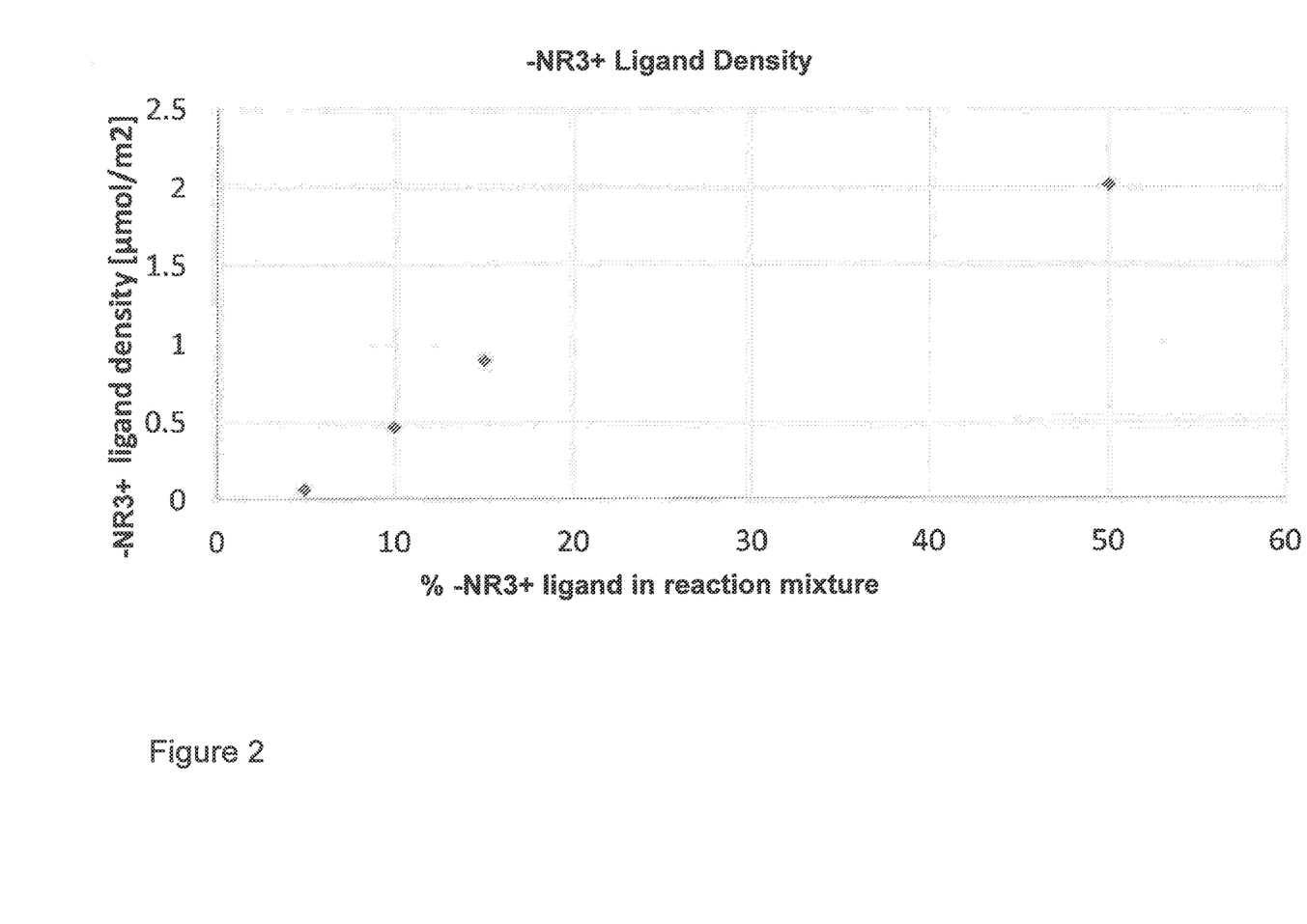
FIG. 2 shows a correlation between cationic functional group ($—NR_3^+$) in the reaction mixture and cationic functional group attached to the silica gel.

The amount of charged groups attached as a function of the concentration in solution and determined by ionic titration is shown in FIG. 1 for the anionic functional group —SO$_3^-$ and in FIG. 2 for the cationic functional group —NR$_3^+$.

The CIEX columns thus prepared have been termed C5 (5% anionic groups in solution), C10 (10% anionic groups in solution), C15 (15% anionic groups in solution), C50 (50% anionic groups in solution), and C100 (100% anionic groups in solution), the neutral column RP (0% ionic groups in solution), and the AIEX columns A5 (5% cationic groups in solution), A10 (10% cationic groups in solution), A15 (15% cationic groups in solution), and A50 (50% cationic groups in solution). The amount of attached charged groups (found by titration) can be derived from FIGS. 1 and 2.

Example 2

A peptide (synthetic peptide 1) with pI between 11 and 12 was subjected to separation with different columns and different ionic strength of the used acetate buffer of pH 4.8 and identical acetonitrile (AcN) gradient of 0.51% by volume/minute, starting at about 19% AcN.

Figure 3A:
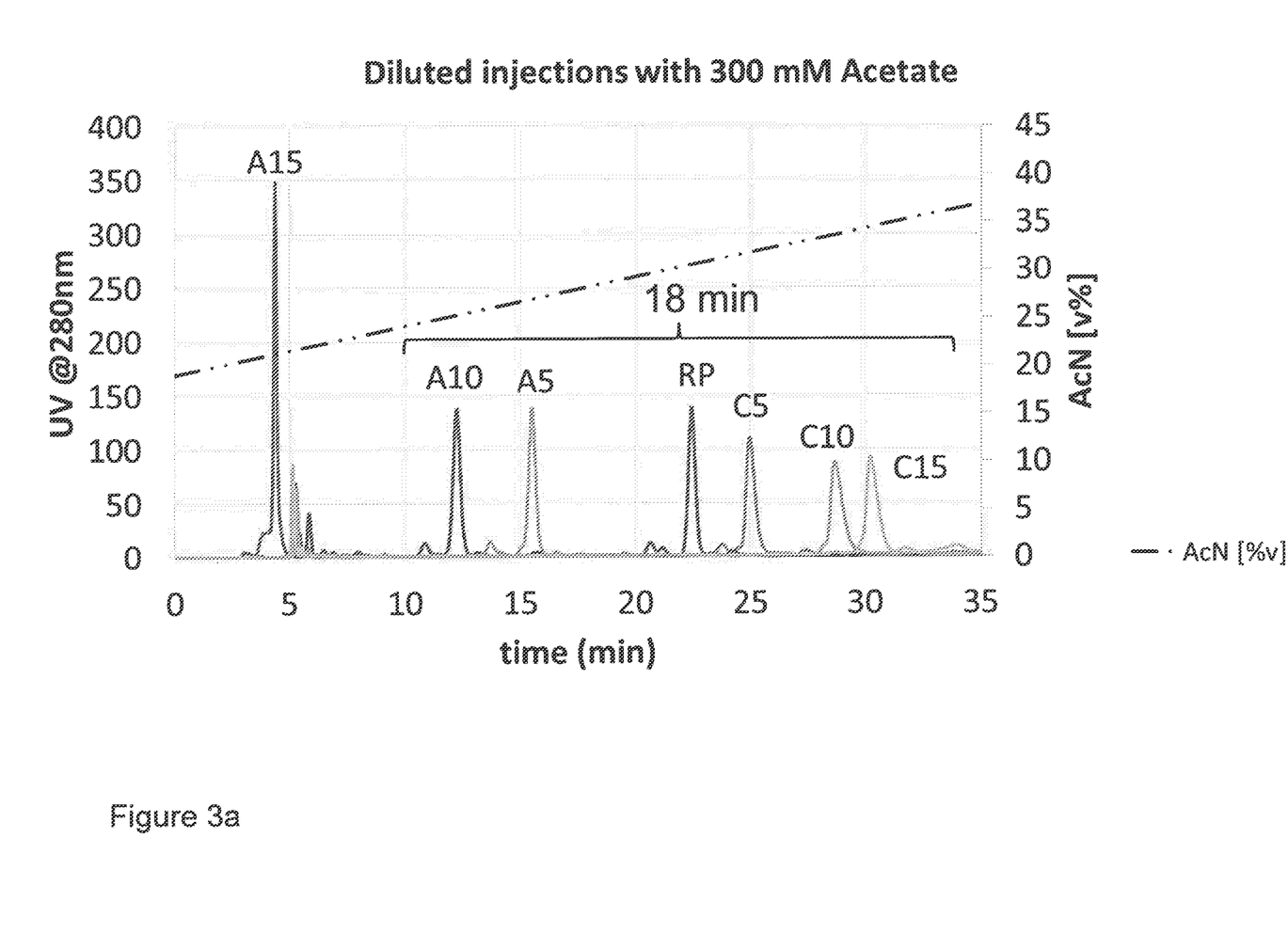
Figure 3B:
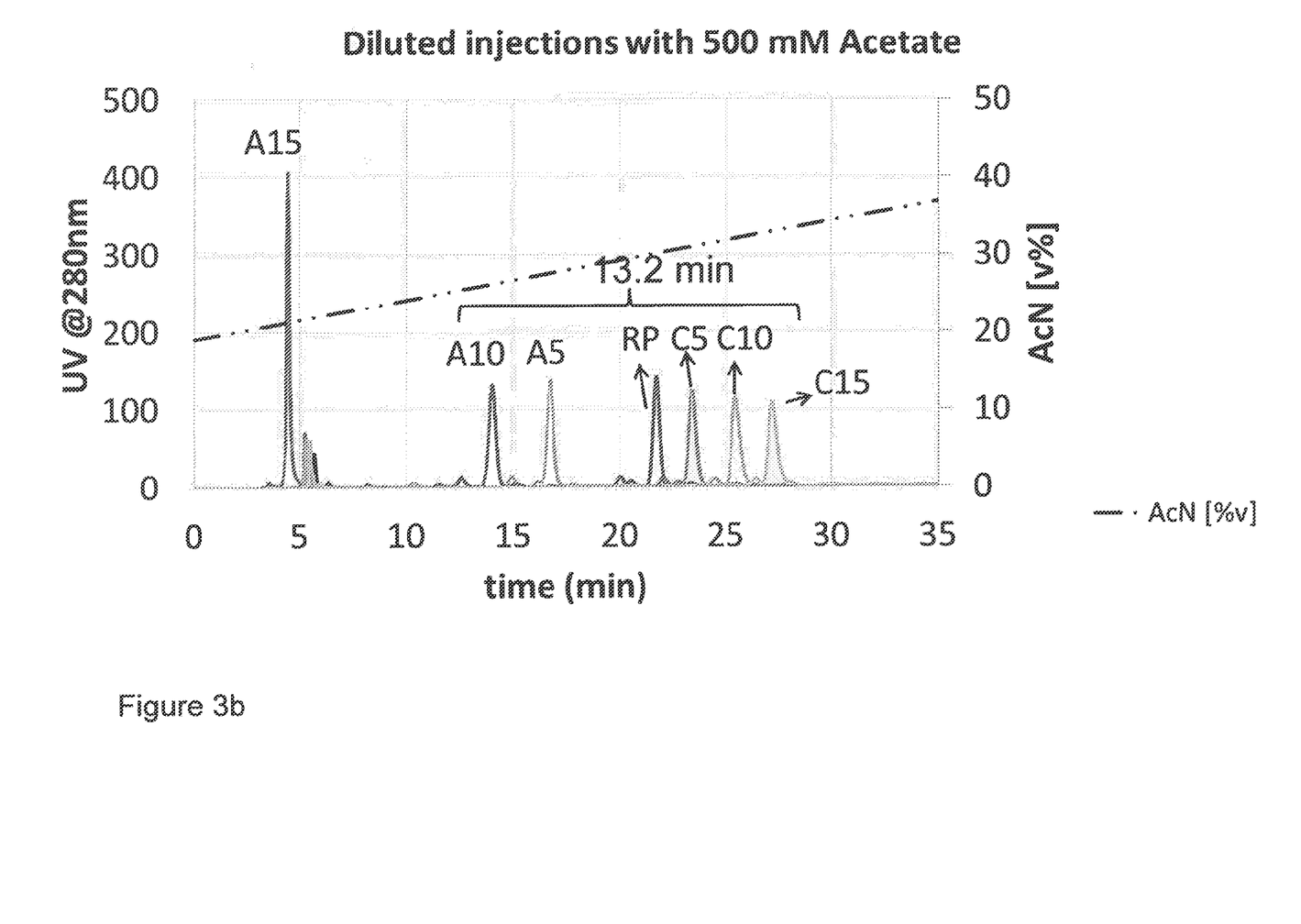
Figure 3C:
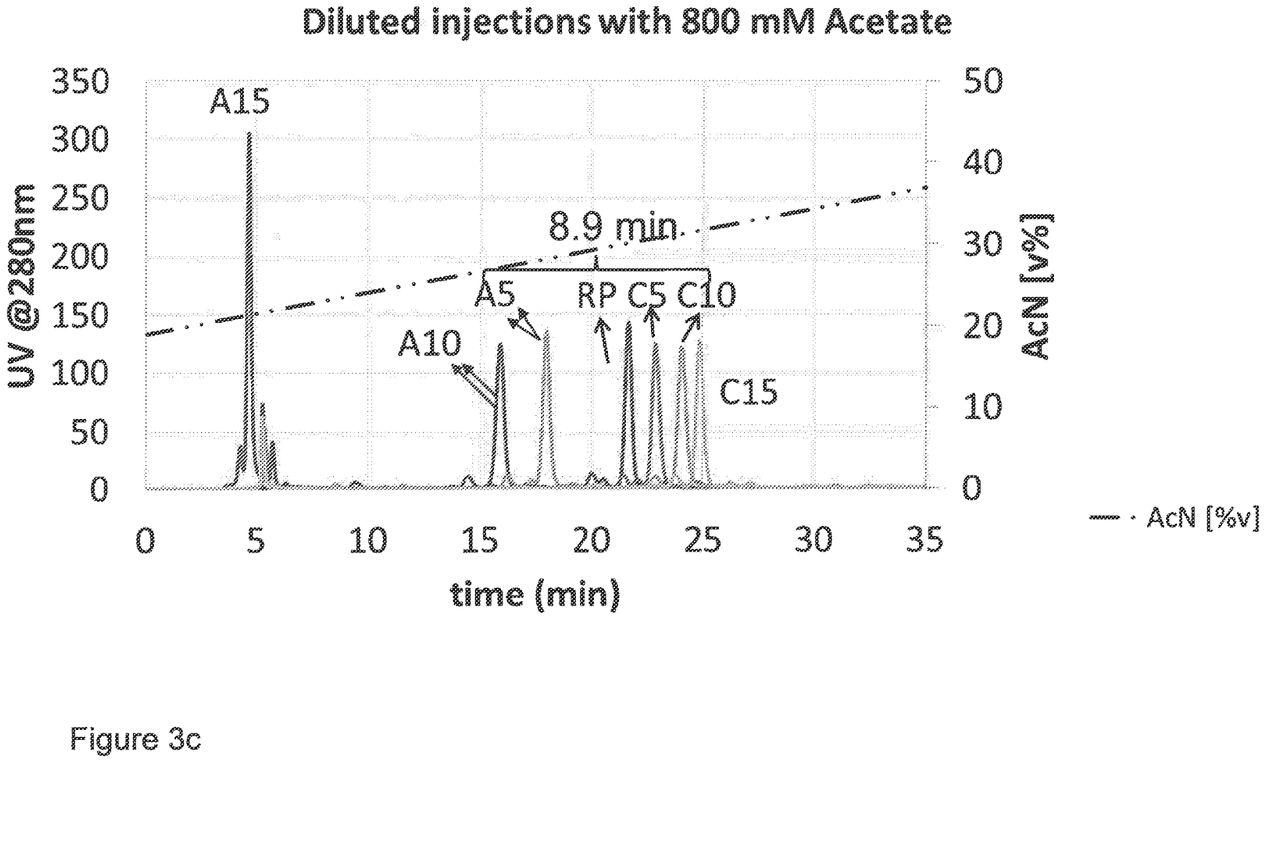

As can be seen from each of the FIGS. 3a to 3c, the adsorption of a positively charged peptide on —NR$_3^+$/C8 materials is low (repulsion) while it is strong on —SO$_3^-$/C8 materials (attraction). Several columns were tested under identical conditions and the retention times compared with each other. As can be seen, the column A15 has almost no adsorption or strong repulsion, respectively, while the material C15 has strong adsorption and thus long retention time. The A15 material is not usable since the peptide of interest does not adsorb while the C15 material is not so good in economic view because the purification process is too slow and requires substantial amount of solvent.

As can be seen from a comparison of FIGS. 3a to 3c, column A15 with about 1 μmol/m$^2$ has not only an undesirably short retention time of less than 5 minutes but it does also not react to the changes in the ionic strength (buffer concentration). This is another piece of evidence that this material is not suitable for the intended use.

Contrary thereto, the less doped materials reacted quite sensitive to the changed reaction conditions making all of them valuable reversed phase materials. By enhancing the buffer concentration from 300 mM acetate to 800 mM acetate the retention time on C15 could be reduced from more than 30 minutes to less than 25 minutes. In addition, at high buffer concentration the retention times of all columns came closer indicating that the salt (acetate) shields the charges such that the doped materials behave similar to the not doped RP material.

As already indicated above, only for column A15 no effect was found. Without wanting to be limited by any interpretation, the inventors assume that this unexpected behaviour may indicate that this material is so repulsing that the buffer concentrations used are not sufficient to overcome this repulsion.

Example 3

In this example the effect of a changed starting concentration and gradient on the retention times of the different columns was investigated. In order to minimize the effect of the buffer salt, only 100 mM acetate buffer was used. Also in this example the API was synthetic peptide 1 with pI of 11 to 12.

The AcN gradient was 0.25% by volume/minute.

Figure 4A:
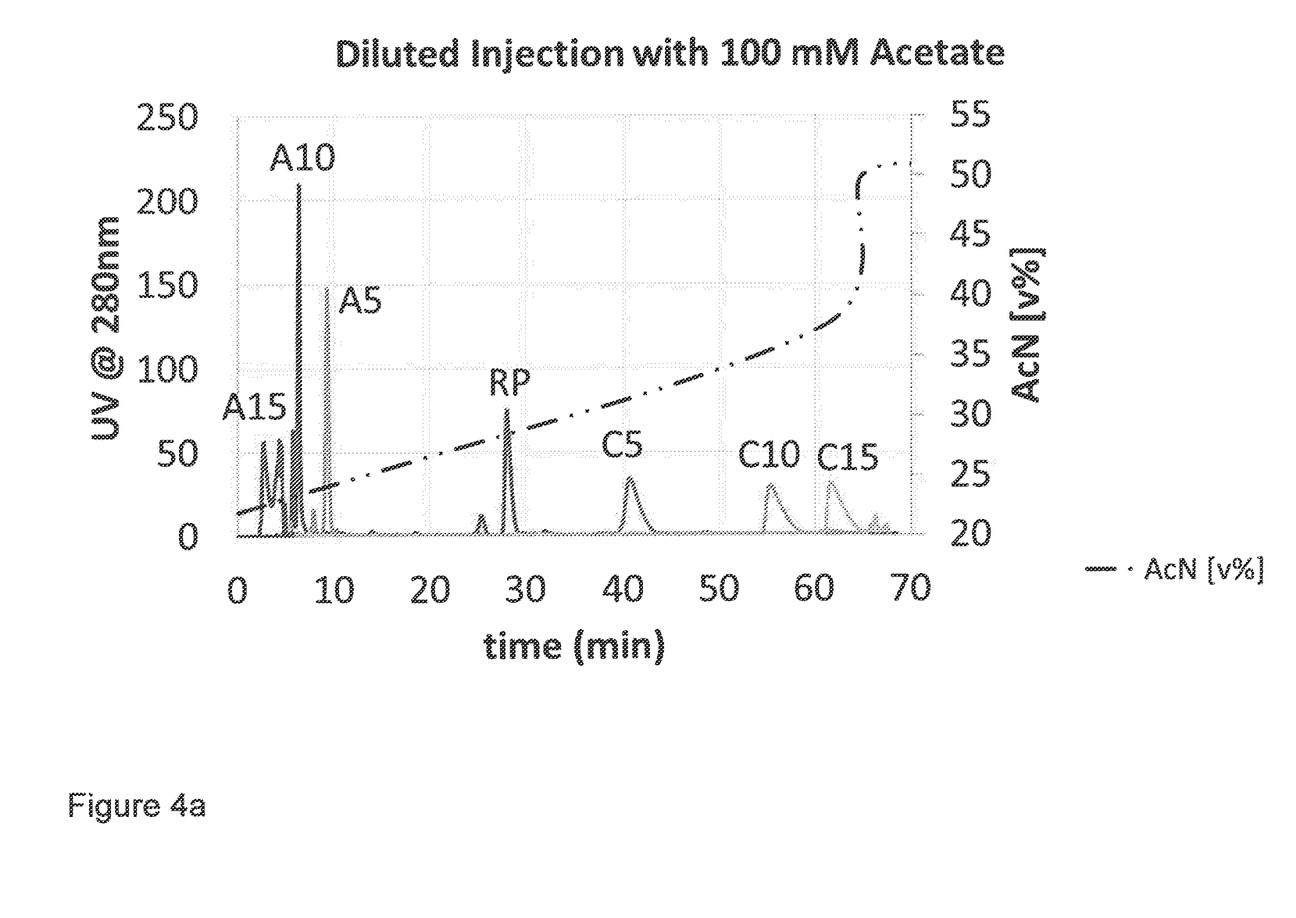
Figure 4B:
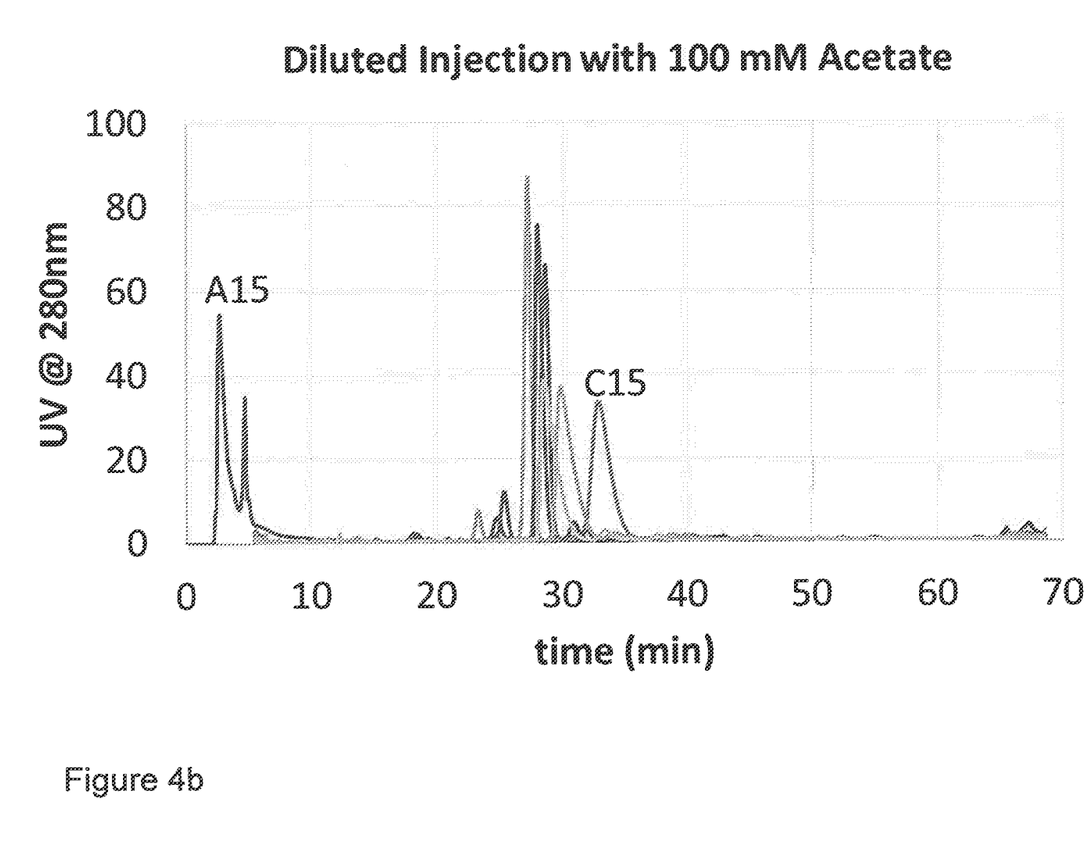
FIG. 4b shows that the retention times can be brought together by varying the initial composition and/or the gradient.

In one experiment, the AcN initial concentration was 22% AcN (see FIG. 4a), in a second experiment the AcN initial concentration was changed to insure retention time t$_R$=30±3 min (FIG. 4b).

As can be seen form a comparison of FIG. 4a with FIG. 4b, the retention times are highly dependent from the initial AcN concentration.

The conditions leading to the results shown in FIG. 4b for all columns are listed in Table 1 below:

TABLE 1

| Column | AcN Start [v %] | AcN End [v %] | gradient time [min] | gradient [v %/min] | retention time [min] |
|---|---|---|---|---|---|
| C15 | 31.7 | 47.3 | 61.2 | 0.25 | 28.5 |
| C10 | 29.5 | 45.1 | 61.2 | 0.25 | 29.8 |
| C5 | 24.2 | 39.8 | 61.2 | 0.25 | 32.8 |
| RP | 21.9 | 37.5 | 62.4 | 0.25 | 28.0 |
| A5 | 14.8 | 30.4 | 61.3 | 0.25 | 27.2 |
| A10 | 10.8 | 26.4 | 61.2 | 0.25 | 28.6 |
| A15 | 6.3 | 21.9 | 61.3 | 0.25 | dead time |

Example 4

The selectivity of the different columns in the separation of insulin/desamido-insulin (insulin pI=5.3) at pH 4.8 and pH 6.8 was investigated. The results are shown in FIG. 5.

The experimental conditions were:
eluent: 240 mM acetate (pH 4.8 or 6.8, respectively) and AcN in an amount to ensure a retention time $t_R$ of insulin of about 32 minutes; and
isocratic elution.

Figure 5:
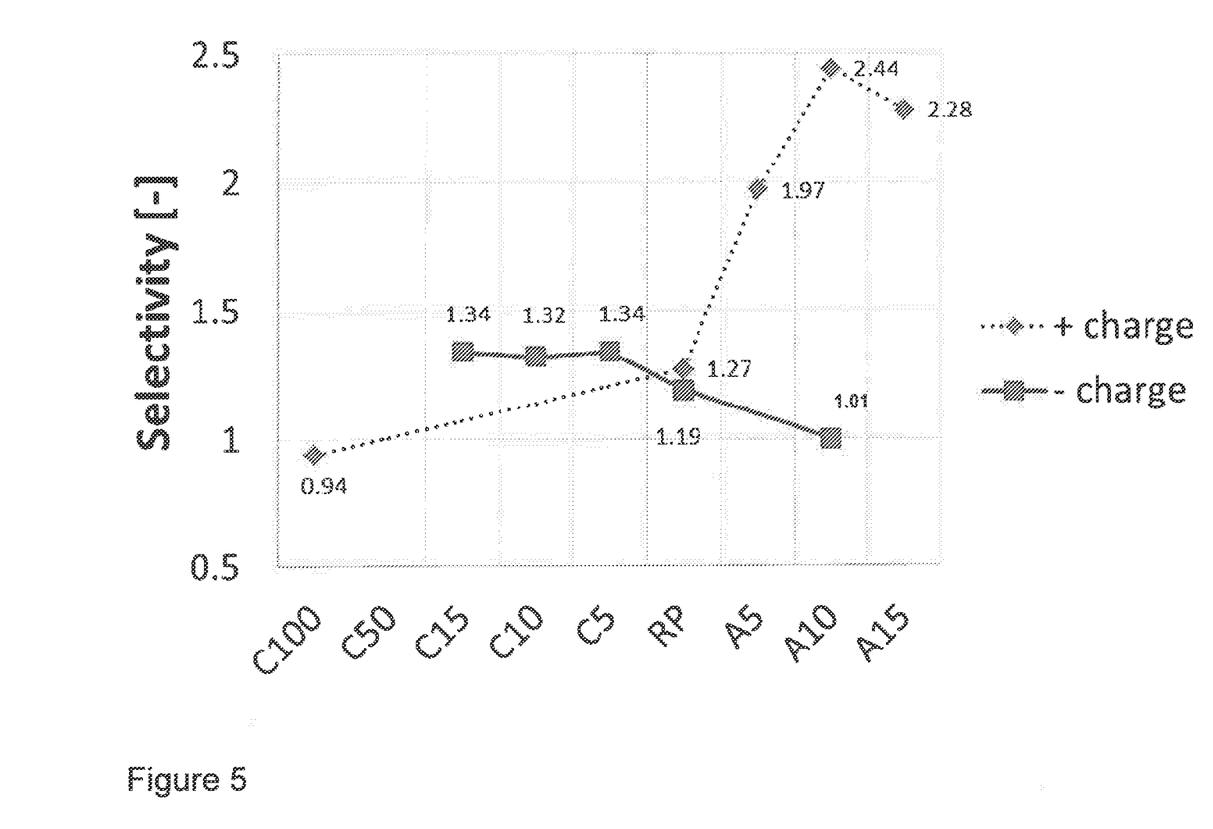
FIG. 5 shows the selectivity for the separation of insulin/desamido-insulin (insulin pI=5.3) on different column materials and at two different pH.

The insulin/desamido-insulin selectivity at pH 4.8 was
S<1 on a CIEX material
S>1 on the RP
S=1 on the CIEX-RP materials
S>>1 on the AIEX-RP materials As can be seen from FIG. 5, at pH 4.8 (•••◆•••) the —NR$_3^+$/C8 materials show much enhanced selectivity compared to the pure C8 material. At higher pH (--■--) the selectivity is inversed. Thus, the repulsing materials are better than the attracting materials, i.e. —SO$_3^-$/C8.

Example 5

This example describes the purification of a synthetic peptide 1 that was selected for a pI between 11 and 12. The pH of the mobile phase was below the peptide pI, i.e. the peptide was positively charged.

The mobile phase was pH=4.8, 500 mM sodium acetate buffer+acetonitrile

The starting concentration and the gradient information is listed in Table 2:

TABLE 2

| Column | AcN Start [v %] | AcN End [v %] | gradient time [min] |
|---|---|---|---|
| C50 | 28.6 | 33 | 80 |
| C5 | 17 | 33 | 80 |
| RP | 15.9 | 32.2 | 80 |
| A5 | 13.9 | 30 | 80 |
| A10 | 11.7 | 26.4 | 80 |

Figure 6:
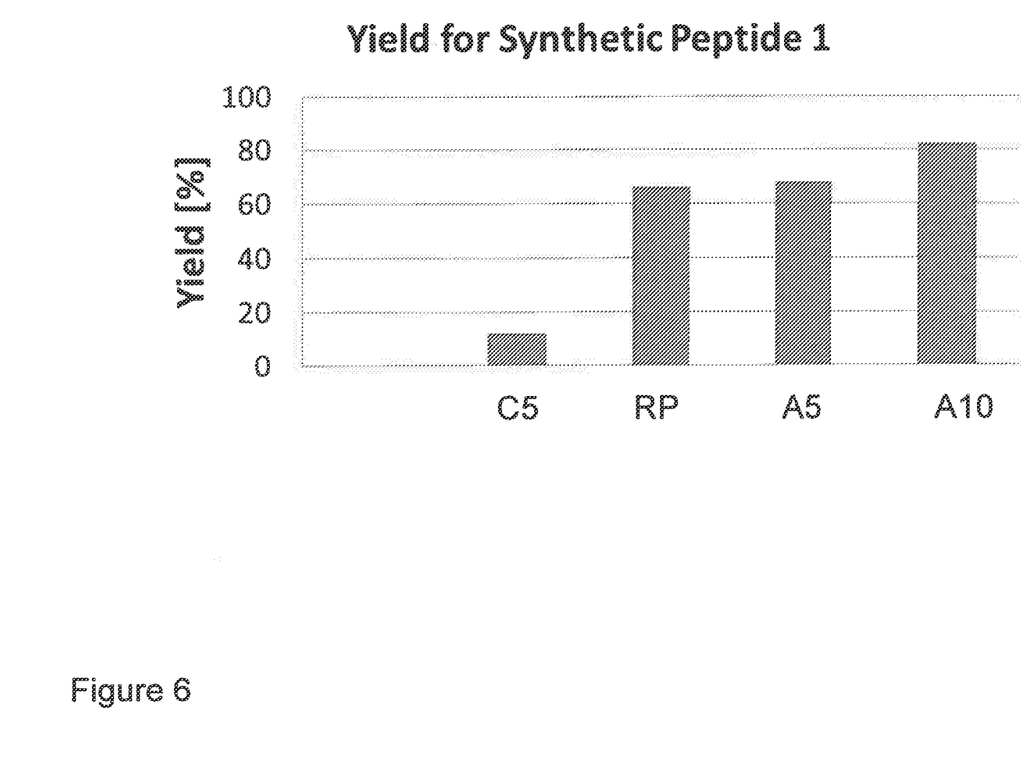
FIG. 6 shows preparative purification of synthetic peptide 1 according to Example 5.

Result: As can be seen from FIG. 6, by using an AIEX-RP material (A10) the yield could be raised for 25% at a fixed purity of 94%.

Example 6

This example describes the purification of a synthetic peptide 2 that was selected for a pI between 9 and 10. The pH of the mobile phase below the peptide pI, i.e. the peptide was positively charged.

The mobile phase was pH=4.8, 120 mM sodium acetate buffer+acetonitrile

The starting concentration and the gradient information are listed in Table 3.

TABLE 3

| Column | AcN Start [v %] | AcN End [v %] | gradient time [min] |
|---|---|---|---|
| C5 | 28.6 | 48.6 | 80 |
| RP | 21.9 | 39.3 | 80 |
| A5 | 17.5 | 35.7 | 80 |
| A10 | 14.8 | 32.2 | 80 |

Figure 7:
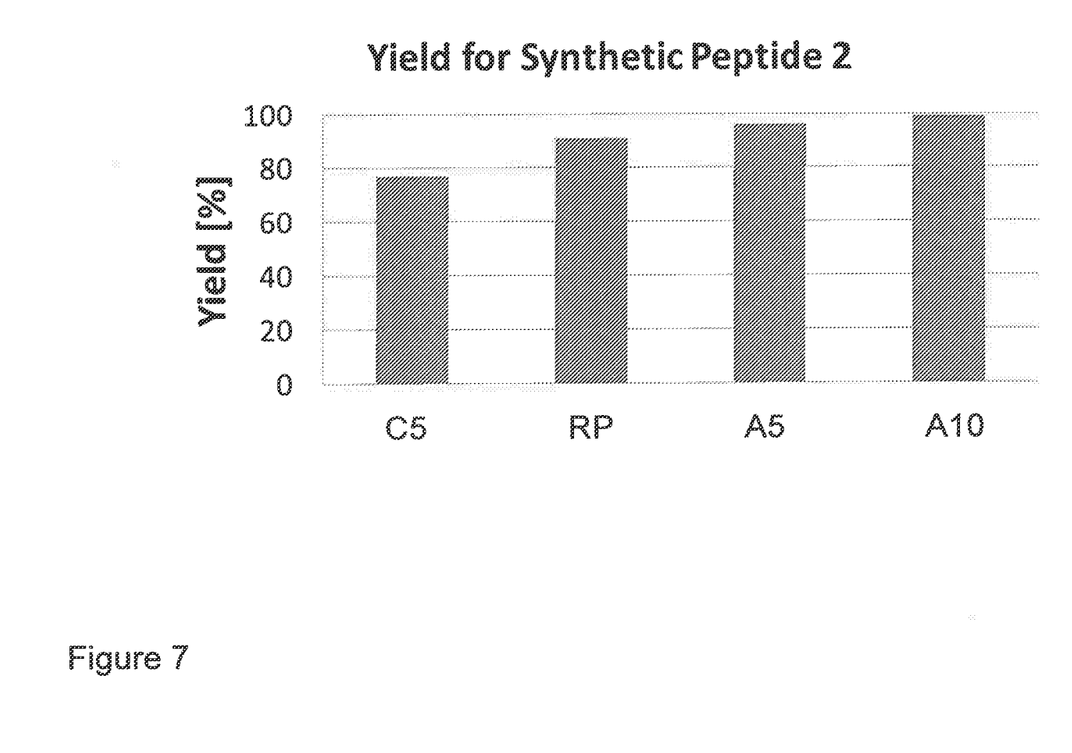
FIG. 7: shows preparative purification of synthetic peptide 2 according to Example 6.

Result: As can be seen from FIG. 7, by using an AIEX-RP material (A10) the yield could be raised for 7.4% at a fixed purity of 94%.

Example 7

This example describes the purification of a synthetic peptide 3 that was selected for a pI between 4.5 and 5.5. The pH of the mobile phase was above the peptide pI, i.e. the peptide was negatively charged.

The mobile phase was pH=6.5, 100 mM ammonium acetate buffer+acetonitrile.

The starting concentration and the gradient information are listed in Table 4.

TABLE 4

| Column | AcN Start [v %] | AcN End [v %] | gradient time [min] |
|---|---|---|---|
| 15C | 20.2 | 34.7 | 60 |
| 10C | 20.2 | 34.7 | 60 |
| 5C | 20.7 | 35.2 | 60 |
| RP | 21.7 | 36.2 | 60 |
| A5 | 24.6 | 39.1 | 60 |
| A10 | 28.4 | 42.9 | 60 |

Figure 8:
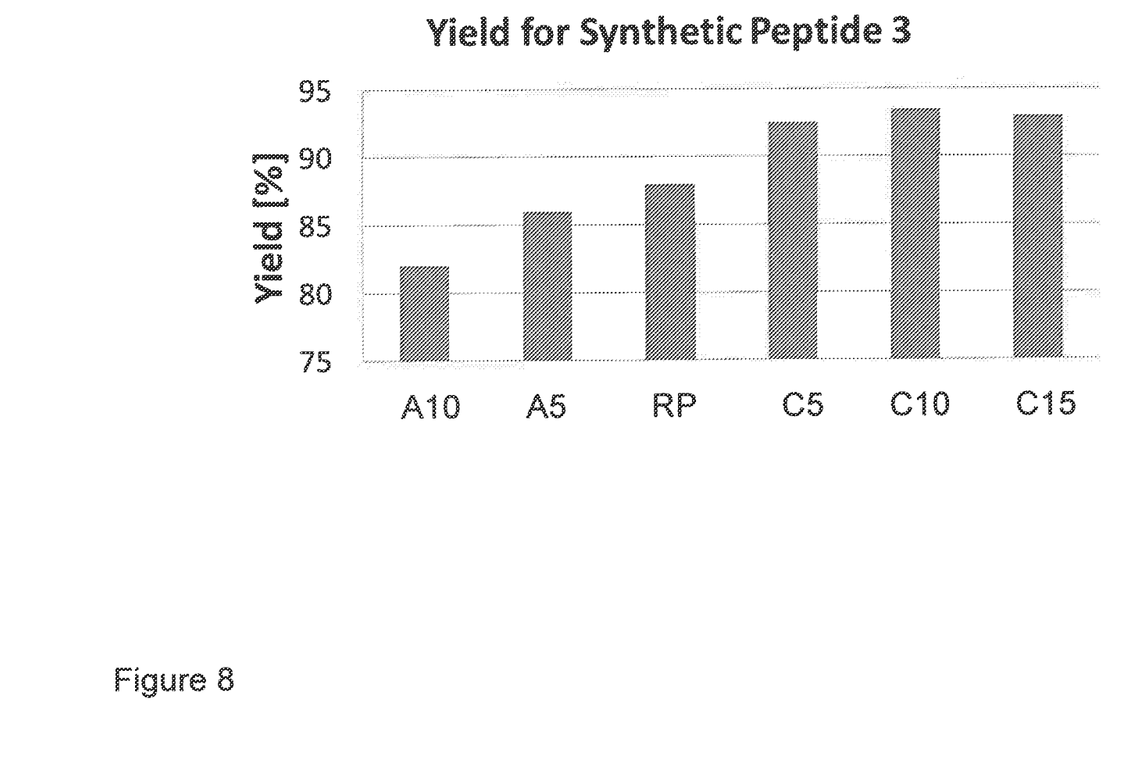
FIG. 8: shows preparative purification of synthetic peptide 3 according to Example 7.

Result: As can be seen from FIG. 8, in this case, due to the negative charge of the API the —SO$_3^-$/C8 materials show better performance. Also here the repulsing materials are better. By using a CIEX-RP material (C10) the yield could be raised for 5.9% at a fixed purity of 87%.

CONCLUSION

All experiments show that repulsingly doped materials have improved performance. This is in contradiction to the general opinion that for improved performance additional adsorption positions have to be created. The present results show that the performance of the materials is improved by creating repulsing positions.

While there are shown and described presently preferred embodiments of the invention, it is to be distinctly understood that the invention is not limited thereto but may be otherwise variously embodied and practiced within the scope of the following claims.

The invention claimed is:

1. A material for reverse phase chromatography comprising surface modifying groups bound to a solid support that is silica gel, wherein said surface modifying groups are not horizontally polymerized, said surface modifying groups comprising apolar uncharged groups and polar groups, and wherein said polar groups being charged groups, said charged groups being either positively charged or negatively charged, and said charged groups being present in amounts of about 0.25 to about 22% of the surface modifying groups, or in amounts of about 0.01 µmol/m$^2$ to 0.8 µmol/m$^2$ referred to the surface of the solid support for a material with a total amount of surface modifying groups of 3.6 µmol/m$^2$, the surface modifying groups being bound to the surface via a reaction of monofunctional silanes carrying the surface modifying groups or trifunctional silanes carrying the surface modifying groups, the positively charged groups being —NR$_3^+$ groups wherein R is selected from hydrogen or C1-C2 alkyl and the negatively charged groups being —SO$_3^-$ groups, the charged groups are terminal substituents of aliphatic C1 to C18 groups, the apolar uncharged groups are linear C4 to C18 alkyl groups, and the aliphatic groups of the charged groups are shorter by up to 6 CH$_2$ groups compared to the length of the apolar groups.

2. A method for a reversed phase chromatographic separation of active pharmaceutical ingredients (APIs), said method comprising evaluating a reversed phase material of claim 1, and API purification conditions by
   (a) determining the isoelectric point (pI) of the API of interest,
   (b) choosing a pH in a range where the solid support material is stable,
   (c) determining the difference of pI–pH and
   (d) if the difference pI–pH is positive (pI>pH), choosing an anion exchange (AIEX) material, or
   if the difference pI–pH is negative (pI<pH), choosing a cation exchange (CIEX) material.

3. The method of claim 2 further comprising the step of
   (e) evaluating a desired retention time by adapting at least one eluting condition.

4. The method of claim 3 wherein the at least one eluting condition comprises the ionic strength of a buffer.

5. The method of claim 3 wherein the at least one eluting condition comprises an eluent system, an initial eluent composition and a gradient.

6. The method of claim 5 wherein the eluent system is an aqueous buffer and acetonitrile.

7. The method of claim 2 wherein the pH is between 3 and 9.

8. A method for producing a material for reverse phase chromatography of claim 1, comprising attaching all surface modifying groups simultaneously from a liquid solution comprising the apolar groups and the polar charged groups.

9. A method for producing a material for reverse phase chromatography of claim 1, comprising a first step, wherein the apolar groups are attached followed by a second step wherein the charged groups are attached or vice versa, wherein the first step is performed such that some available silanol groups are not reacted.

10. The material of claim 1, wherein the apolar uncharged groups comprise C8 groups and the charged groups comprise C3 groups.

11. The material of claim 1, wherein the charged groups are —NR3+ and wherein R is methyl.

12. The material of claim 1, wherein the silica gel has a porosity of 50 to 300 Å, and particle sizes from 5 to 100 µm.

13. The material of claim 12, wherein the silica gel has a porosity of about 100 Å, and particle sizes from 10 to 20 µm.

14. The method of claim 2, wherein the active pharmaceutical ingredients (APIs) comprise peptides.

15. The method of claim 7, wherein the pH is between 4 and 7.

16. The method of claim 8, wherein the method comprises determining the amount of apolar and ionic groups attached to the material.

17. The method of claim 9, wherein the attached ionic groups are determined.

18. The material of claim 1, wherein the aliphatic groups of the charged groups are shorter than the apolar groups by up to 5 CH$_2$ groups.

19. The material of claim 1, wherein the aliphatic groups of the charged groups are shorter than the apolar groups by 3 to 5 CH$_2$ groups.

20. The material of claim 1, wherein the monofunctional silanes carrying the surface modifying groups are monochlorosilanes.

21. The material of claim 1, wherein the trifunctional silanes carrying the surface modifying groups are trichlorosilanes or trimethoxysilanes.

* * * * *